United States Patent
Marino et al.

(10) Patent No.: US 10,292,688 B2
(45) Date of Patent: May 21, 2019

(54) REMOVABLE BONE PENETRATING DEVICE AND METHODS

(71) Applicant: Trinity Orthopedics, LLC, San Diego, CA (US)

(72) Inventors: James F. Marino, La Jolla, CA (US); Jamil Elbanna, San Diego, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 246 days.

(21) Appl. No.: 15/101,370

(22) PCT Filed: Dec. 2, 2014

(86) PCT No.: PCT/US2014/068222
§ 371 (c)(1),
(2) Date: Jun. 2, 2016

(87) PCT Pub. No.: WO2015/084881
PCT Pub. Date: Jun. 11, 2015

(65) Prior Publication Data
US 2016/0302777 A1 Oct. 20, 2016

Related U.S. Application Data

(60) Provisional application No. 61/911,977, filed on Dec. 4, 2013.

(51) Int. Cl.
*A61B 10/02* (2006.01)
*A61B 17/16* (2006.01)
*A61B 17/32* (2006.01)

(52) U.S. Cl.
CPC ........ *A61B 10/025* (2013.01); *A61B 10/0275* (2013.01); *A61B 17/1604* (2013.01);
(Continued)

(58) Field of Classification Search
CPC .............. A61B 10/025; A61B 17/1604; A61B 10/0275; A61B 2010/0208; A61B 2017/320064
See application file for complete search history.

(56) References Cited

U.S. PATENT DOCUMENTS 3,628,524 A 12/1971 Jamshidi
3,893,445 A 7/1975 Hofsess
(Continued)

FOREIGN PATENT DOCUMENTS

| JP | 2001-521406 A | 11/2001 |
|---|---|---|
| WO | WO-91/06246 A1 | 5/1991 |
| WO | WO-97/39685 A1 | 10/1997 |

OTHER PUBLICATIONS

"Trap It." HS Hospital Service. Web. Sep. 2, 2016. http://www.hshospitalservice.com//prod.php?id=116.
(Continued)

*Primary Examiner* — Sean P Dougherty
(74) *Attorney, Agent, or Firm* — Mintz Levin Cohn Ferris Glovsky and Popeo, P.C.

(57) ABSTRACT

Disclosed are embodiments of a removable tip device, which include a bone penetration feature at a distal end and a securing feature that allows the removable tip device to be removably secured to a distal end of various embodiments of a bone coring device. Some embodiments of the removable tip device include features that assist in transmitting torsional loads from the bone coring device to the bone removal feature. In addition, some embodiments of the removable tip device include a protective element that is configured to provide a protective surface for a distal feature of the bone coring device.

14 Claims, 16 Drawing Sheets

(52) U.S. Cl.
CPC .............. *A61B 2010/0208* (2013.01); *A61B 2017/320064* (2013.01)

(56) References Cited

U.S. PATENT DOCUMENTS

| | | | |
|---|---|---|---|
| 4,403,617 A * | 9/1983 | Tretinyak | A61B 10/025 |
| | | | 600/567 |
| 4,789,547 A | 12/1988 | Song et al. | |
| 4,793,363 A | 12/1988 | Ausherman et al. | |
| 4,951,690 A * | 8/1990 | Baker | A61B 17/1695 |
| | | | 128/898 |
| 5,040,542 A | 8/1991 | Gray | |
| 5,106,364 A | 4/1992 | Hayafuji et al. | |
| 5,341,816 A | 8/1994 | Allen | |
| 5,505,210 A * | 4/1996 | Clement | A61B 10/04 |
| | | | 600/566 |
| 5,526,822 A | 6/1996 | Burbank et al. | |
| 5,649,547 A | 7/1997 | Ritchart et al. | |
| 5,730,752 A | 3/1998 | Alden et al. | |
| 5,769,086 A | 6/1998 | Ritchart et al. | |
| 5,807,277 A | 9/1998 | Swaim | |
| 5,833,628 A * | 11/1998 | Yuan | A61B 10/025 |
| | | | 600/567 |
| 6,063,037 A | 5/2000 | Mittermeier et al. | |
| 6,139,509 A | 10/2000 | Yuan et al. | |
| 6,248,081 B1 | 6/2001 | Nishtalas et al. | |
| 6,383,145 B1 * | 5/2002 | Worm | A61B 10/0266 |
| | | | 600/564 |
| 6,554,778 B1 | 4/2003 | Fleming, III | |
| 7,033,324 B2 | 4/2006 | Giusti et al. | |
| 7,179,232 B2 | 2/2007 | Sutton et al. | |
| 9,192,396 B2 | 11/2015 | Marino | |
| 10,039,601 B2 * | 8/2018 | Kim | A61B 18/1815 |
| 2001/0005778 A1 | 6/2001 | Ouchi | |
| 2001/0009978 A1 | 7/2001 | Krueger et al. | |
| 2001/0014778 A1 * | 8/2001 | Worm | A61B 10/0266 |
| | | | 600/564 |
| 2003/0229293 A1 | 12/2003 | Hibner et al. | |
| 2004/0049128 A1 * | 3/2004 | Miller | A61B 10/025 |
| | | | 600/566 |
| 2004/0059252 A1 * | 3/2004 | Giusti | A61B 10/025 |
| | | | 600/562 |
| 2004/0077973 A1 | 4/2004 | Groenke et al. | |
| 2005/0107800 A1 | 5/2005 | Frankel et al. | |
| 2005/0251063 A1 | 11/2005 | Basude | |
| 2006/0247653 A1 | 11/2006 | Akerfeldt et al. | |
| 2007/0282220 A1 | 12/2007 | Abernathie | |
| 2007/0293788 A1 | 12/2007 | Entrekin et al. | |
| 2008/0161720 A1 * | 7/2008 | Nicoson | A61B 10/0275 |
| | | | 600/567 |
| 2010/0152616 A1 | 6/2010 | Beyhan et al. | |
| 2013/0144188 A1 | 6/2013 | Fiebig et al. | |

OTHER PUBLICATIONS

International Search Report issued in PCT/US2014/068222 dated Feb. 24, 2015.

* cited by examiner

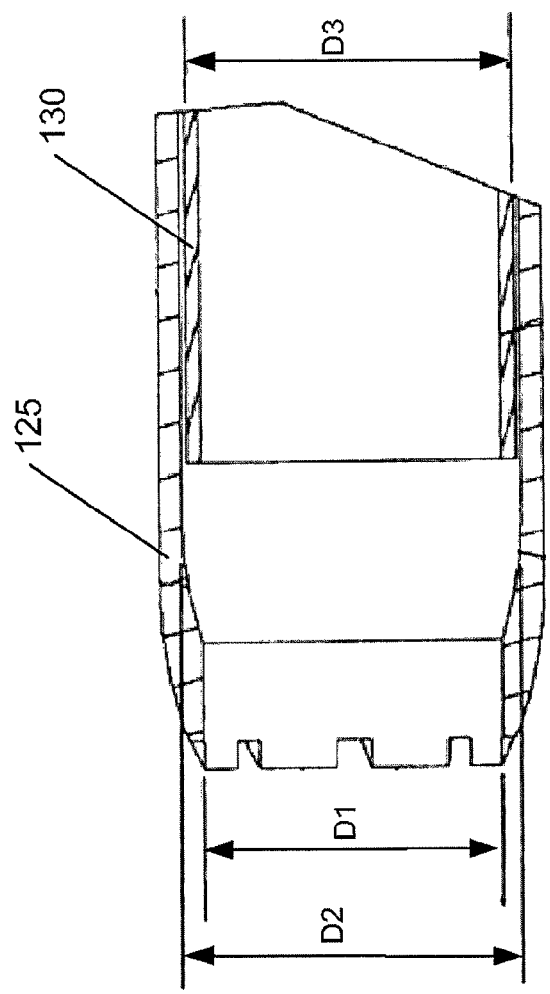

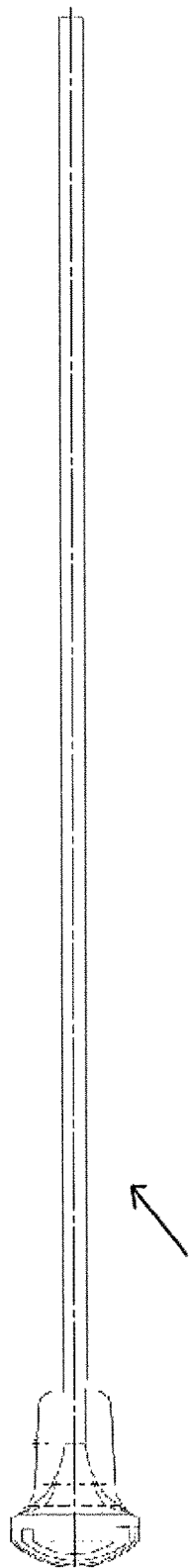

REMOVABLE BONE PENETRATING DEVICE AND METHODS

CROSS-REFERENCE TO RELATED APPLICATION

This application is a national stage application, filed under 35 U.S.C. § 371, of International Application No. PCT/US2014/068222, filed on Dec. 2, 2014, entitled "Removable Bone Penetrating Device and Methods," which claims priority to U.S. Provisional patent application No. 61/911,977, filed on Dec. 4, 2013, entitled "Removable Bone Penetrating Device and Methods," the contents of which are hereby incorporated by reference in its entirety.

BACKGROUND

It is often necessary to access a core sample of biological material such as to diagnose defects or ailments. To obtain a sample, an instrument may be used to remove a portion or a "core sample" from surrounding biological material. In some circumstances, the cored material is cancellous bone. For example, it may be desirable for a physician to access decorticated bone and then retrieve cancellous bone for grafting or other purposes.

SUMMARY

Aspects of the current subject matter can include a bone coring device, including removable devices that can be adapted to the bone coring device, such as a removable tip device.

In one aspect, a removable tip device is disclosed that can include a bone penetration feature configured to penetrate a layer of bone and a securing feature configured to releasably engage a distal end of a bone coring device.

In another aspect, a method of using the removable tip device can include providing a removable tip device for securing to a distal end of a bone coring device. The removable tip device can include a bone penetration feature configured to penetrate a layer of bone, and a securing feature can be configured to releasably engage a distal end of a bone coring device. In addition, the method can include engaging the securing feature of the removable tip device to the distal end of the bone coring device.

In some variations one or more of the following can optionally be included in any feasible combination. For example, the method can include penetrating a layer of bone with the bone penetration feature, and the layer of bone can include cortical bone. The securing feature can include a push button or tab configured to releasably engage a fenestration along the distal end of the bone coring device. The fenestration can be configured to minimize movement of the engaged securing feature relative to the fenestration for assisting in transmitting torsional loads from the bone coring device to the bone penetration feature.

In addition, the removable tip device can include a deformable element that extends from the securing feature and assists in at least one of engaging and disengaging the securing feature to the distal end of the bone coring device. The deformable element can include an asymmetric cross-sectional geometry that is configured to transmit torsional loads from the bone coring device to the bone penetration feature. Additionally, the removable tip device can include a protective element configured to provide a protective surface for a distal feature of the bone coring device. The protective element can include an o-ring made out of a compliant material. Furthermore, the removable tip device can include an outer sleeve configured to stabilize the removable tip device relative to the bone coring device at least when a torsional load or a longitudinal load is applied to the bone coring device.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

These and other aspects will now be described in detail with reference to the following drawings.

FIG. 9 shows a cross-sectional view of the distal region of the coring assembly with the inner tube positioned within the outer cutting tube.

FIG. 10 shows a side view of a tamping member that interfaces with the core sample device.

Like reference symbols in the various drawings indicate like elements.

DETAILED DESCRIPTION

Figure 1:
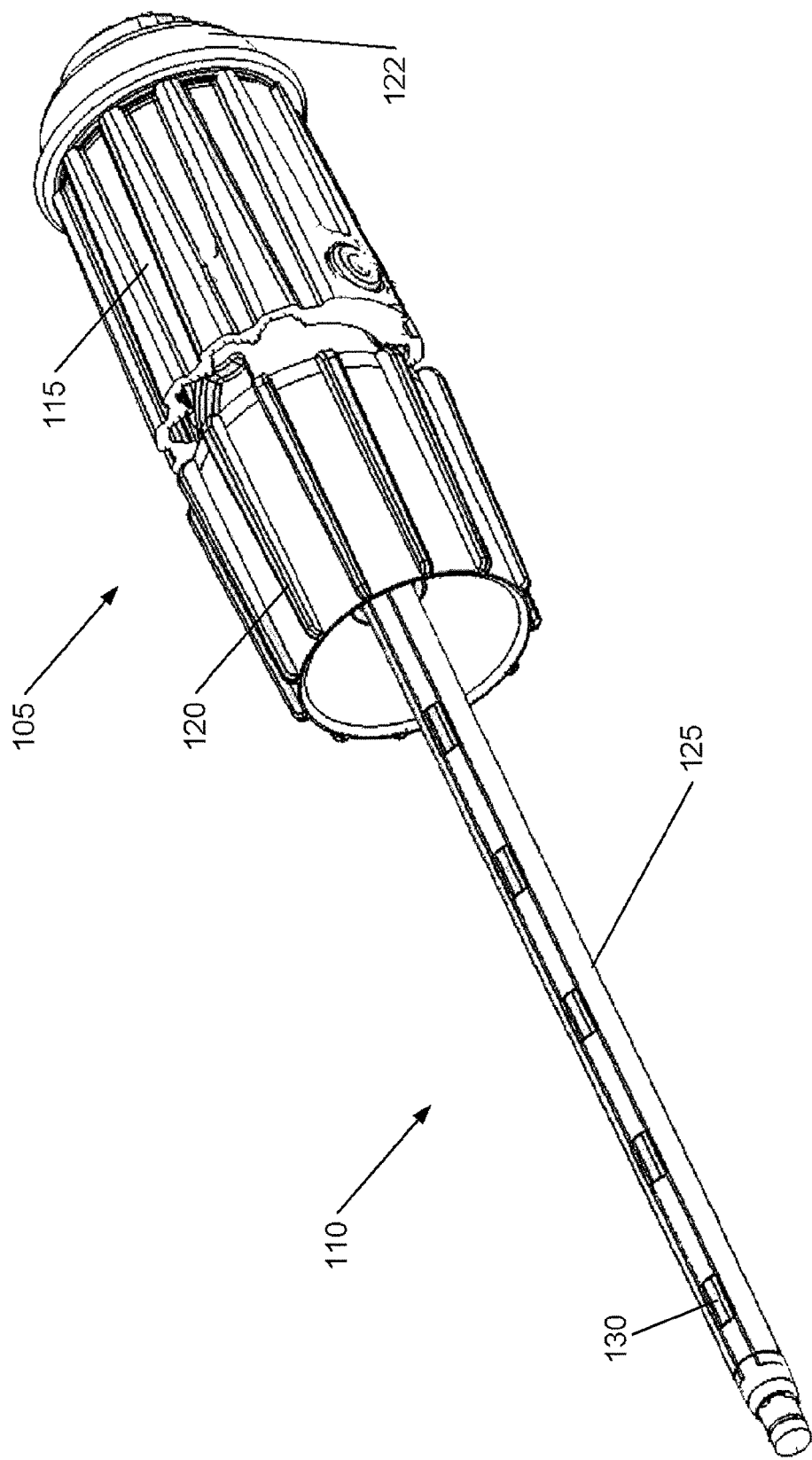
FIG. 1 shows a perspective view of a core sample device that is adapted to remove one or more core samples of bone tissue.

FIG. 1 shows a perspective view of a core sample device that is adapted to remove one or more core samples of tissue, such as bone tissue. The device includes a handle 105 that can be grasped by a user to hold and manipulate the device. The handle 105 is coupled to a cutting or coring assembly 110 that can be advanced into a material to be sampled, such as bone material, for retrieving a core sample of the material, as described in detail below. In an embodiment, the handle 105 serves as an actuator that is actuated to cause a first portion of the coring assembly 110 to move relative to a second portion of the coring assembly 110 to cut the material to be sampled. In this regard, the coring assembly 110 includes an outer cutting tube 125 and an inner tube 130 that is movably positioned concentrically within the outer cutting tube 125.

With reference still to FIG. 1, the handle 105 has a generally cylindrical shape that is adapted to fit within the hand of a user. As mentioned, the handle 105 can serve as an actuator that causes relative movement between components of the coring assembly 110. In this regard, the handle 105 includes a first handle component 115 and a second handle component 120 that is movably coupled to the first handle component 115. In an exemplary embodiment, the first handle component 115 is positioned at a proximal end of the device and the second handle component 120 is positioned distally of the first handle component 115. A cap 122 is positioned at a proximal-most region adjacent the first handle component 115. It should be appreciated that the relative positions of the first 115 and second 120 handle components can vary and that the shape of the handle 105 and its components can also vary, such as to provide ergonomic features.

The first handle component 115 (the proximal component) can be rotated relative to the second handle component 120 (the distal component) to cause relative movement between the outer cutting tube 125 and the inner tube 130 of the coring assembly 110. For example, rotational movement of the first handle component 115 relative to the second handle component 120 causes the inner tube 130 to linearly move or translate relative to the outer cutting tube 125, as described more fully below. In this regard, the inner tube 130 linearly translates along an axis that coincides with the long axis of the coring assembly 110. Various mechanisms can be used to achieve such relative movement of the coring assembly components, some of which are described herein.

Figure 2:
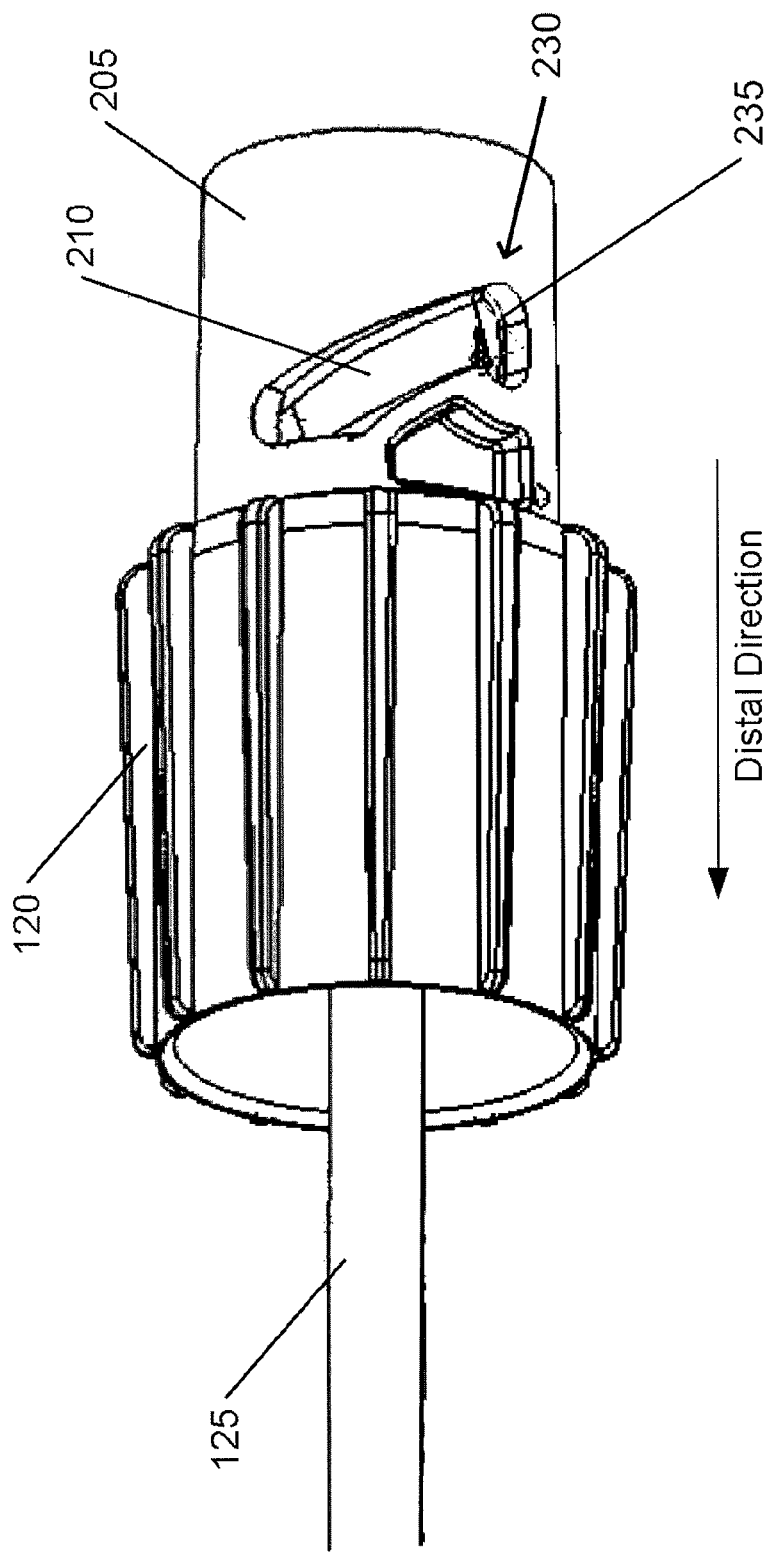
FIG. 2 shows an enlarged view of a second handle component and a portion of an outer cutting tube of the device.

FIG. 2 shows an enlarged view of the second handle component 120 and a portion of the outer cutting tube 125. FIG. 2 does not show the first handle component 115. The outer cutting tube 125 is attached to an interior region of the second handle component 120. The second handle component 120 has a tubular coupling region 205 that enables the first handle component 115 to be rotatably and translationally fixed to the second handle component 120. One or more inclined guide tracks 210 are positioned on the coupling region 205. The inclined guide track 210 slidably mates with a corresponding coupling component (such as one or more mating projections or pins, such as pin 505 shown in FIG. 5A) of the first handle component 115 when the components are coupled to one another. The guide track 210 can have a spiral or partial spiral shape that winds around the outer surface of the coupling region 205.

Figure 4:
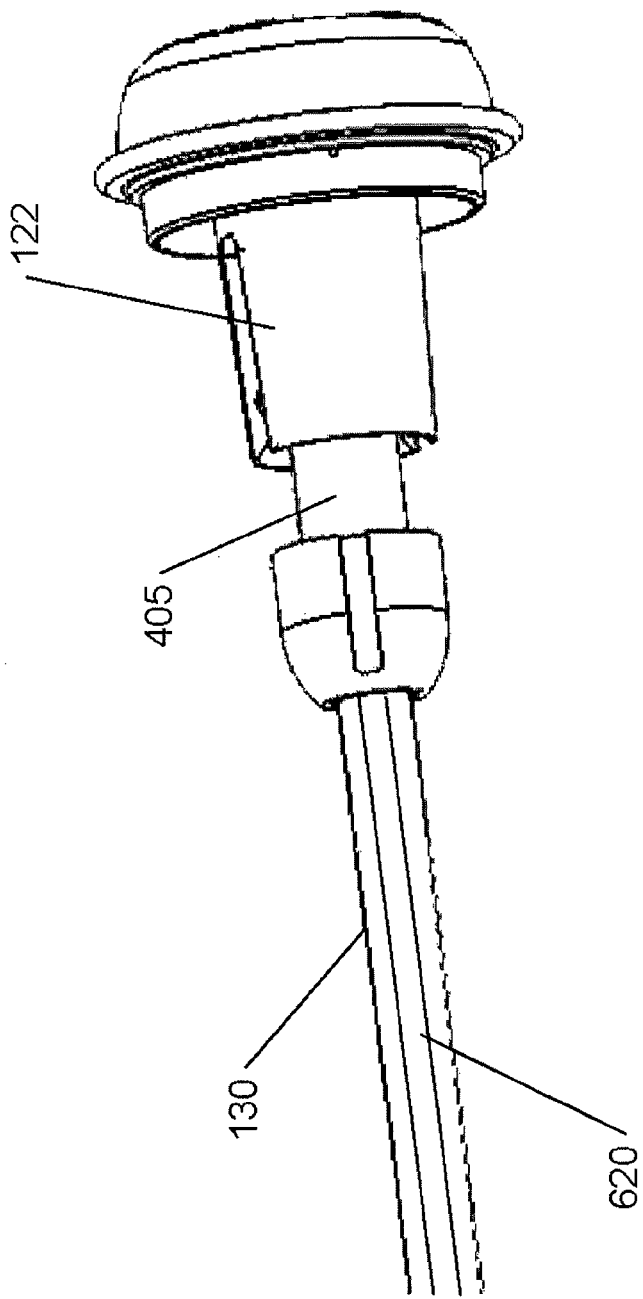
FIG. 4 shows the inner tube associated with a slip plane coupler and a cap.

For example, as the first handle component 115 is rotated, the engagement of the coupling component (such as pin 505) with the guide track 210 can result in linear and rotational translation of the handle component 115 relative to the second handle component 120. In this manner, the guide track 210 can serve as a linkage and the slip plane coupler 405 (shown, for example, in FIG. 4) can assist in transforming the rotational movement of the first handle component 115 relative to the second handle component 120 into a corresponding linear translation motion of the inner element 130 relative to the outer cutting tube 125 along a longitudinal axis of the device. In an embodiment, the outer cutting tube 125 and the inner tube 130 do not rotate relative to one another.

The guide track 210 can have one or more features that enable locking of the handle components 115 and 120 into predetermined states, such as open and closed states (described below). For example, at the proximal-most end 230 of the guide track 210, a projecting element or detent feature 235, such as a snap detent, can be located that locks the handle components 115 and 120 relative to one another. Any quantity of detent features 235 can be located along the length of the guide track 210 to reversibly lock the handle components 115 and 120 relative to each other in a variety of positions.

As mentioned, the guide track 210 in the second handle component 120 slidably mates with one or more inwardly projecting elements, or coupling components, associated with the first handle component 115 to form a force coupling therebetween. Rotation of the first handle component 115 relative to the second handle element 120 results in sliding movement of the projecting element(s) within the guide track 210. The guide track 210 can have a detent feature 235, such as a seat or projection, which interferes with movement of the mating projection at the upper and lower ends of the track 210 to impart resistance to movement. In an embodiment, the resistance to movement induces a palpable and/or audible snap, as well as transitional lock in the open and closed states.

In an embodiment, the track 210 has a recess or seat on the lower surface of the proximal-most end 230 of the track 210. A compressive load (imparted with downward or distal-directed pressure on the proximal first handle component 115 during introduction of the bone harvester into the bone) causes the mating projection of the first handle component 115 to nest into the recess. This results in coupled rotational movement of the first (proximal) handle component 115 and the second (distal) handle component 120 when a distal-directed load is applied to the first handle component 115. As a result, the second lower handle component 120 and first handle component 115 can rotate in unison when both a distally-directed force and rotation is applied to the first handle component 115 (or the associated cap 122).

The depth of the recess can be less than the diameter of the mating projection such that when the distal-directed force is reduced and/or the rotational force of first handle component 115 relative to second handle component 120 increases the mating projection rides up over the recess and along the spiral tract. This terminates the coupled rotation between the first and second handle components 115, 120 and results in linear movement of the inner tube 130 relative to the outer cutting tube 125 such as toward a closed position. This mechanism permits the operator to effectively rotate both the first and second handle components 115 and 120 while applying distal pressure on the first handle component 115 or cap 122, and also while maintaining the relationship of inner slit tube 130 relative to the outer cutting tube 125 with the device in an open state (described below). The operator can then relax the distal-directed force and rotate the first handle component 115 relative to the second handle component 120 to transition from the open locked position to the locked closed position, which can linearly advance the slit tube 130 relative to the outer cutting tube 125.

A similar but reverse oriented mechanism, such as a recess on the upper portion of the distal-most end of the guide track 210, can be used to lock the instrument in a closed position during withdrawal of the instrument. Additionally or alternatively, a snap detent feature may be employed for the same purpose. For example, when a proximal-directed force is applied to the first handle component 115, the mating projection of the first handle component 115 can nest into the recess of the distal-most end of the guide track 210 such that coupled rotational movement of the first (proximal) handle component 115 and the second (distal) handle component 120 is achieved.

Figure 3:
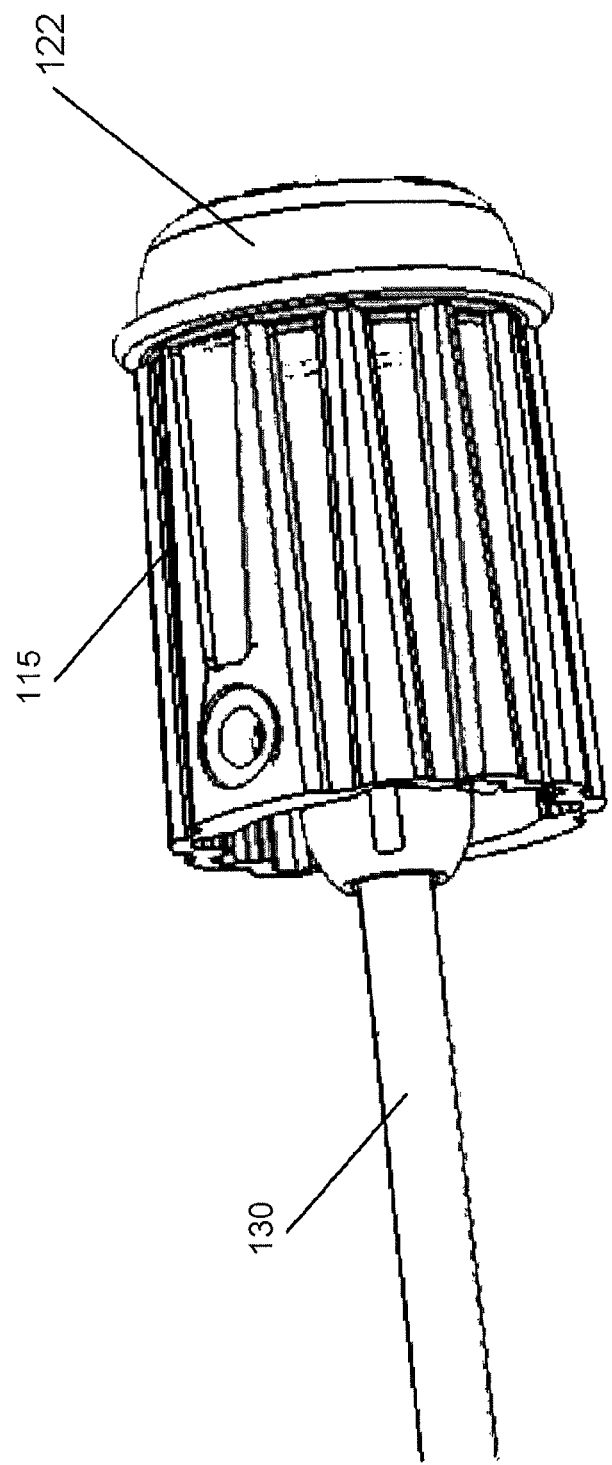
FIG. 3 shows an enlarged view of a first handle component and a portion of the inner tube of the device.

FIG. 3 shows an enlarged view of the first handle component 115 and a portion of the inner tube 130. For clarity of illustration, FIG. 3 does not show the second handle component 120. As mentioned, the first handle component 115 is positioned and secured adjacent to a cap 122. The inner tube 130 is affixed to the slip plane coupler 405, which is associated with a slip plane mating feature of cap 122, with the cap 122 fixed to the first handle component 115. This is described in more detail with reference to FIG. 4, which shows the inner tube 130 and the cap 122 without the first handle component 115. The inner tube 130 has a proximal slip plane coupler 405 that mates with a portion of the cap 122 such that the inner tube 130 is attached to the cap 122.

Linear movement of the cap 122 (along the longitudinal axis of the device) is translated into corresponding linear movement of the inner tube 130. Thus, linear or rotational movement of the first handle component 115, which is secured to the cap 122, translates to corresponding linear movement of the inner tube 130. In addition, the slip plane coupler 405 is rotationally coupled to the second handle component 120 in a manner that permits longitudinal translation of the slip plane coupler 405 and the inner tube 130 relative to second handle component 120. This can result from rotational and translational movement of the first handle component 115 and slip plane mating feature of the cap 122 relative to the second handle component 120.

Figure 5A:
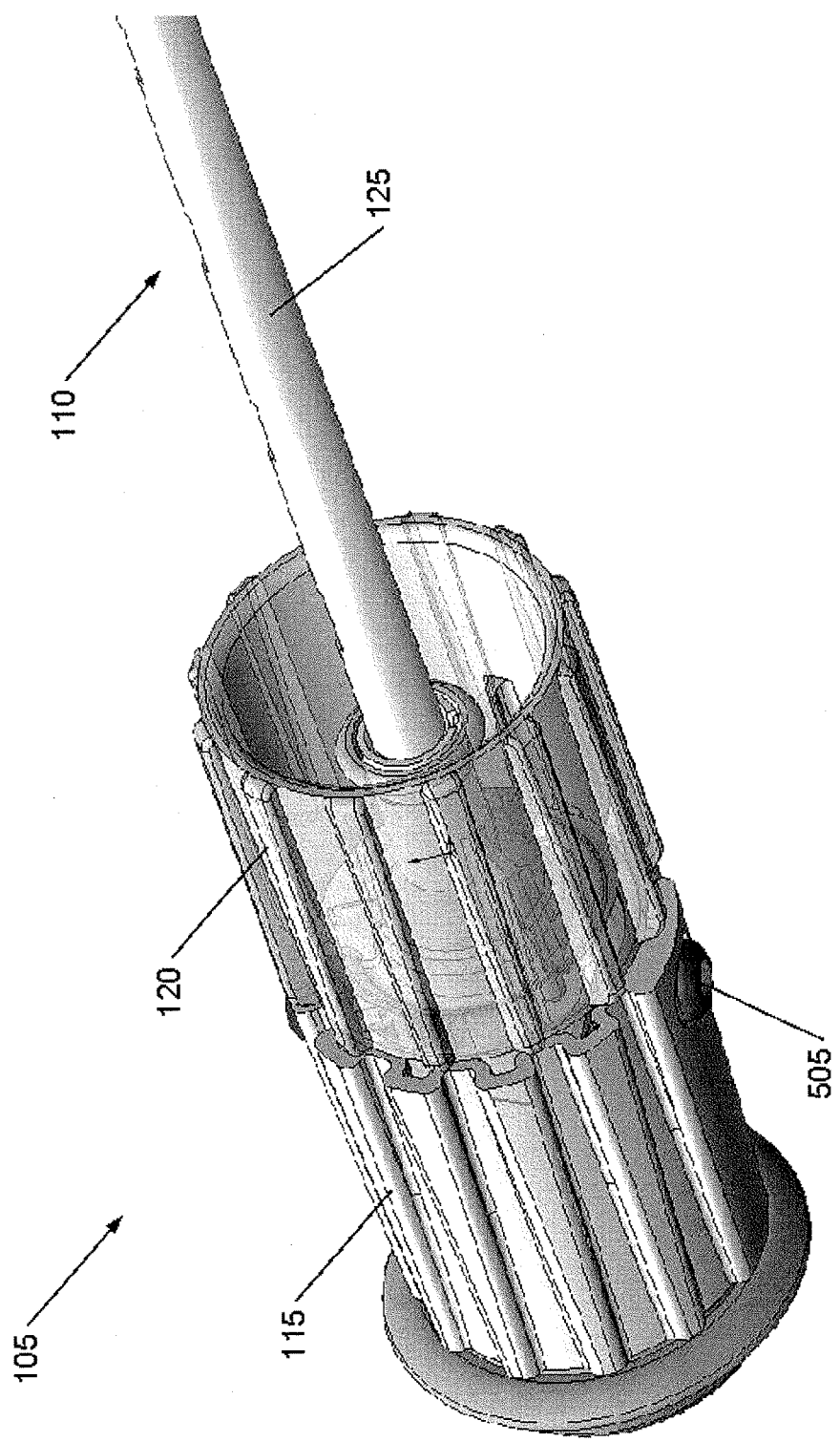
FIG. 5A shows a perspective view of the handle and a portion of the coring assembly while the device is in a "closed" state.
Figure 5B:
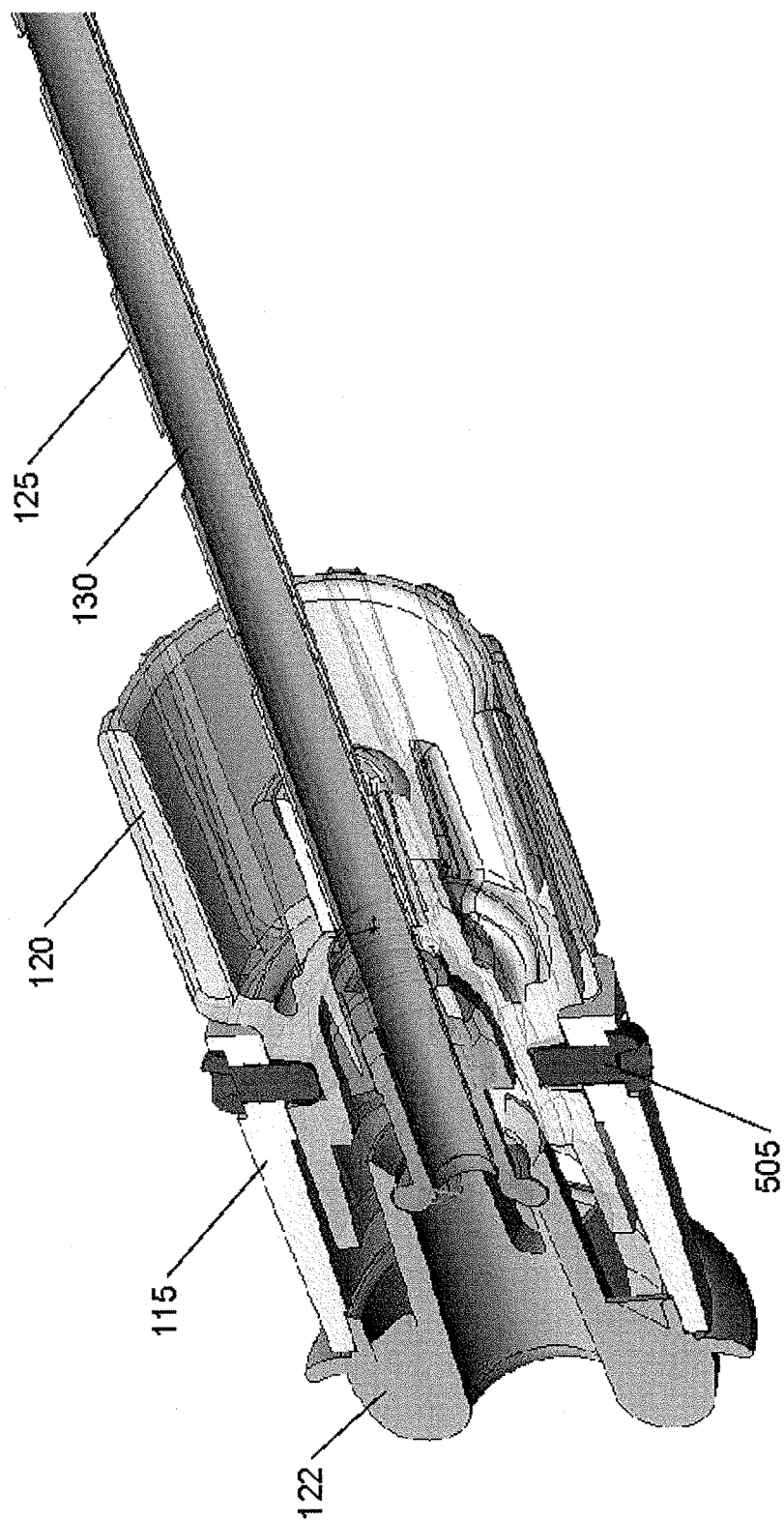
FIG. 5B shows a cross-sectional view of the device while in the closed state.

An exemplary manner in which linear translation of the inner tube 130 is achieved is now described with reference to FIGS. 5A-5D. FIG. 5A shows a perspective view of the handle 105 and a portion of the coring assembly 110 while the device is in a "closed" state. FIG. 5B shows a cross-sectional view of the device while in the closed state. In the closed state, the first handle component 115 is positioned immediately adjacent the second handle component 120, which means that the distal edge of the inner tube 130 is positioned at or near the distal edge of the outer cutting tube 125. In other words, the inner tube 130 is translated distally relative to the longitudinal axis of the device when the device is positioned in the closed state, as described more fully below.

A pair of pins 505 or another coupling structure extend through the first handle component 115 and into the guide tracks 210 (FIG. 2) in the second handle component 120. When the device is in the closed state, the pins 505 can be located at the distal most location of the inclined guide tracks 210. As mentioned, the guide track 210 can have one or more detents 235 that lock the device in the closed state or the open state. As mentioned, the outer cutting tube 125 is attached to the second handle component 120, while the inner tube 130 is associated with the cap 122 via the proximal slip plane coupler 405.

Figure 5C:
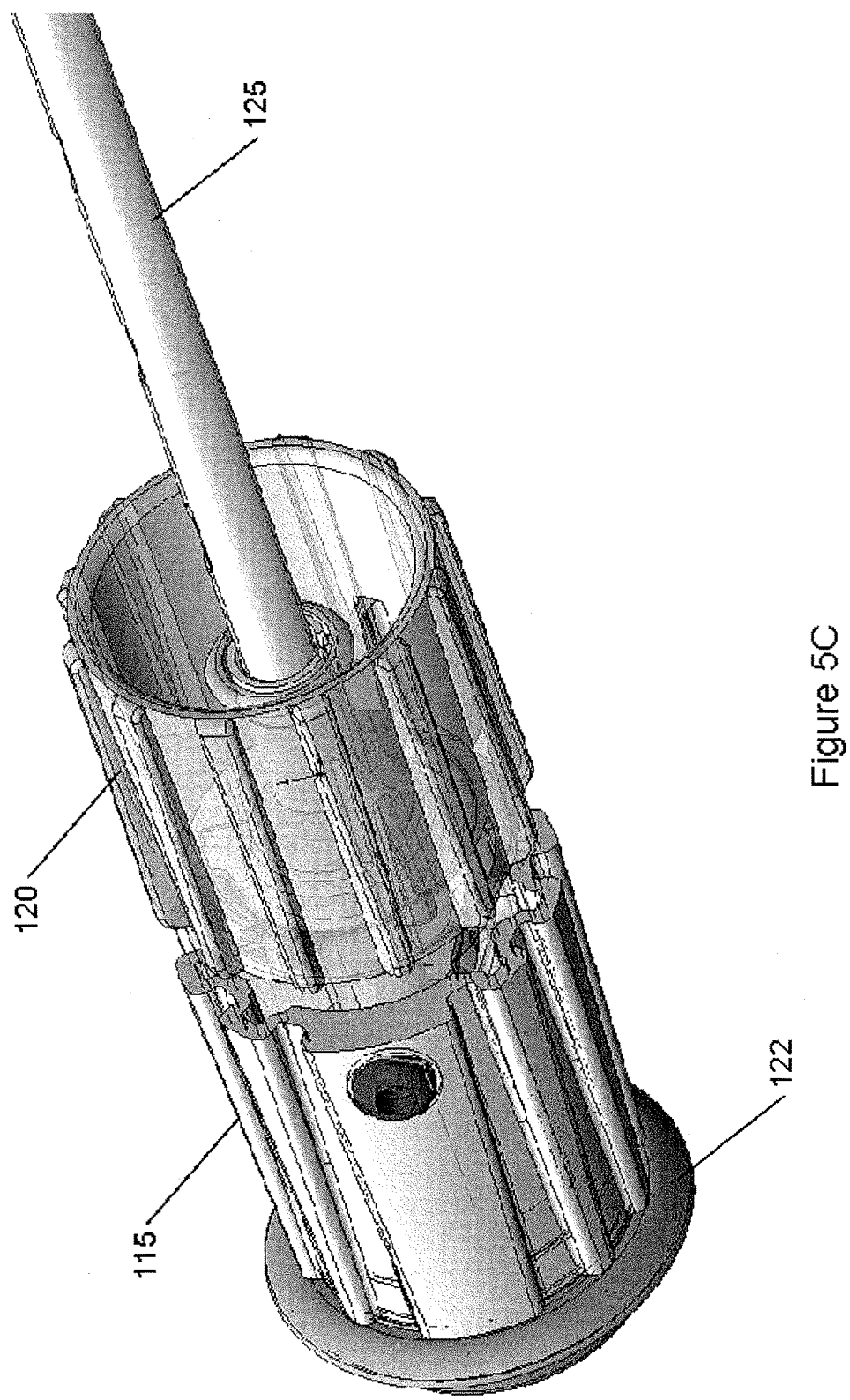
FIG. 5C shows the device in an "open" state that is achieved by rotating the first handle component relative to the second handle component.
Figure 5D:
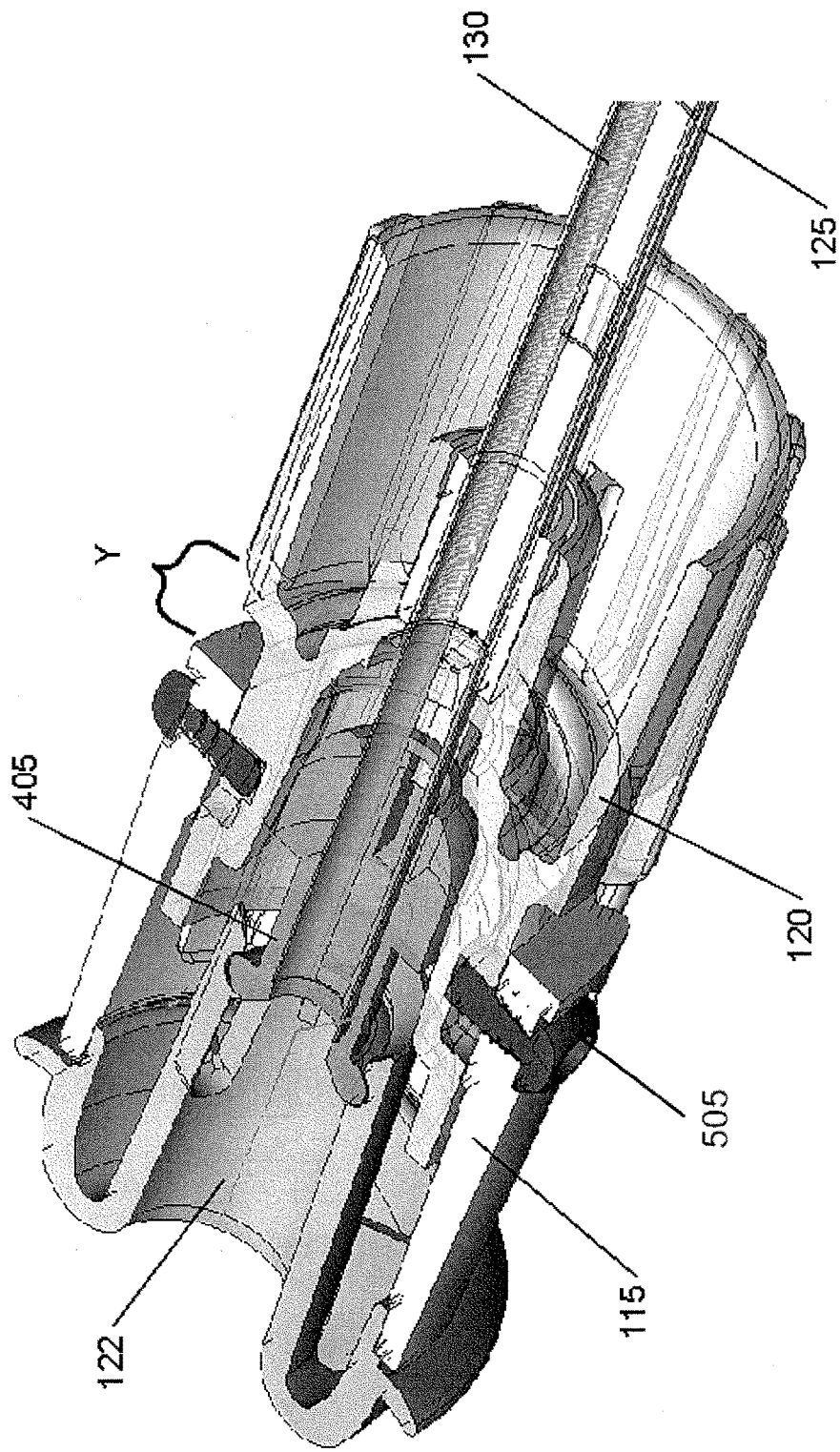
FIG. 5D shows a cross-sectional view of the device while in the open state.

FIG. 5C shows the device in an "open" state that is achieved by rotating the first handle component 115, such as counterclockwise, relative to the second handle component 120. FIG. 5D shows a cross-sectional view of the device while in the open state. In an embodiment, the device transitions to the open state from the closed state by rotating the first handle component 115 about a 90 degree rotation. It should be appreciated, however, that various amounts of rotation can achieve the transition from a closed to an open state, and vice versa.

As mentioned, rotation of the first handle component 115 relative to the second handle component 120 results in linear translation of the inner tube 130 in a proximal direction relative to the longitudinal axis of the device. Thus, in the open state, the distal edge of the inner tube 130 is positioned in a proximal position relative to the longitudinal axis of the device. When in the open state, the device can harvest a sample of tissue, as described more fully below. The linear translation is the result of the linkage (via the guide track 210) between the first handle component 115 and the second handle component 120 via the inclined guide track 210 (as shown in FIG. 2), as well as the relationship of the slip plane coupler 405 relative to the second handle component 120 and the cap 122. Note that in the open state, the first handle component 115 is spaced from the second handle component 120 by a distance Y (as shown in FIG. 5D) as a result of the linear translation. The linear translation along the distance Y has also caused the cap 122 to linearly translate along the distance Y. Because the cap 122 is attached to the inner tube 130 (via the slip plane coupler 405), the inner tube 130 also linearly translates relative to the outer cutting tube 125, which is attached to the second handle component 120. In this manner, linear translation of the inner tube 130 relative to the outer cutting tube 125 is achieved. It should be appreciated that other mechanisms can be used.

Figure 6:
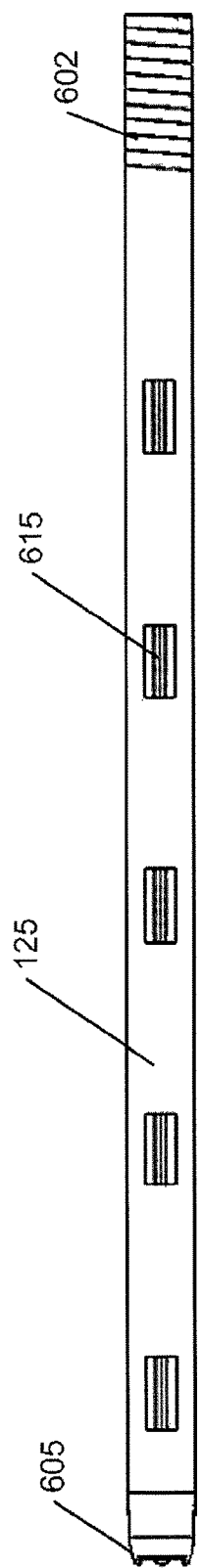
FIG. 6 shows a side view of the outer cutting tube.

The configurations of the outer cutting tube 125 and the inner tube 130 are now described in more detail. FIG. 6 shows a side view of the outer cutting tube 125, which is tubular in shape with a hollow internal shaft that runs the length of the outer cutting tube 125. As mentioned, a proximal region 602 of the outer cutting tube 125 attaches to the second handle component 120 in the assembled device. A series of fenestrations 615 are positioned along the length of the outer cutting tube 125. The fenestrations 615 essentially provide windows into the internal shaft of the outer cutting tube 125 that can assist in viewing of the contents of the tubes, as described below.

Figure 7:
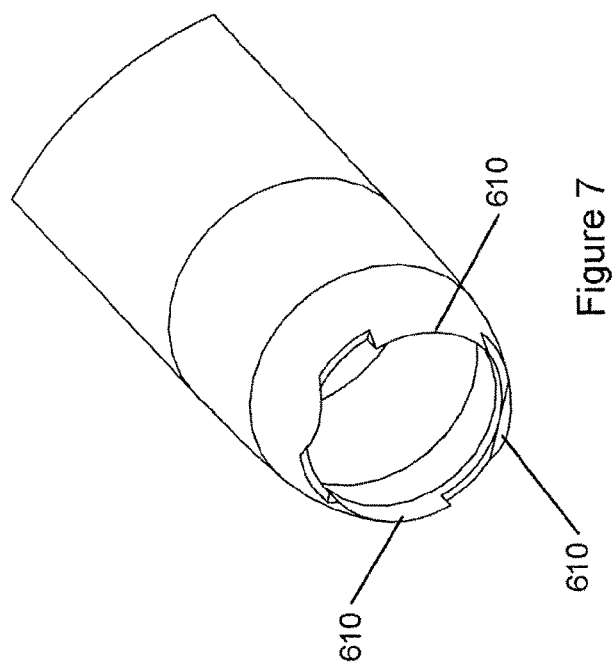
FIG. 7 shows an enlarged view of a distal region of the outer cutting tube.

A distal edge 605 of the outer cutting tube 125 is adapted for cutting or otherwise penetrating through the material being cored, such as through bone. In this regard, the distal edge 605 can be sharpened. FIG. 7 shows an enlarged view of an exemplary embodiment of the distal region 605 of the outer cutting tube 125. A series of teeth 610 are positioned at the distal end 605 of the outer cutting tube 125. The teeth 610 can be arranged in a saw-tooth pattern or in a castellated pattern to grind or micro-fracture cancellous bone via an oscillating or rotational application. The distal teeth 610 can have a raked configuration to reduce potential for bone collecting between the teeth, which could potentially make the teeth less effective in cutting through the bone.

Figure 8:
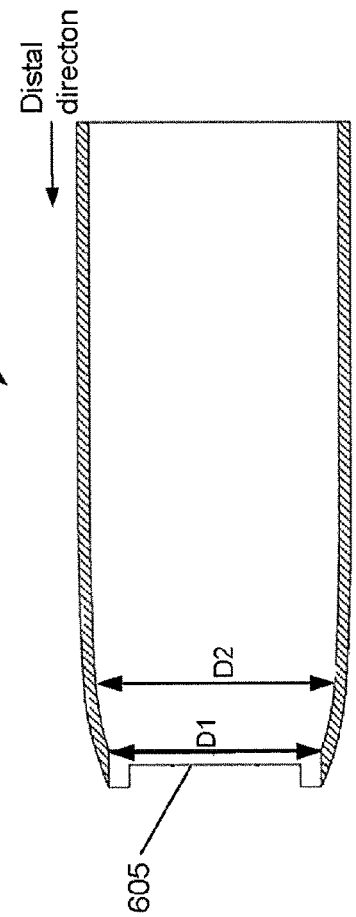
FIG. 8 shows a cross-sectional view of the distal region of the outer cutting tube.

FIG. 8 shows a cross-sectional view of the distal region 605 of the outer cutting tube 125. The external wall of the outer cutting tube 125 is tapered such that the outer diameter gradually decreases moving in the distal direction. The distal taper can reduce potential for penetrating cortical walls of bone with glancing contact during use of the device, as described below. Proximal of the distal edge 605, the internal diameter of the outer cutting tube 125 has an internal taper, which can have a diameter that decreases from D2 to D1 moving toward the distal edge 605.

With reference again to FIG. 4, the inner tube 130 is an elongated tube that is sized to fit concentrically within the internal shaft of the outer cutting tube 125. An elongated slot 620 extends along the entire length or along a portion of the length of the inner tube 130. The slot 620 is aligned with the fenestrations 615 of the outer cutting tube 125 in the assembled device to assist in viewing of the contents of the tubes.

FIG. 9 shows a cross-sectional view of the distal region of the coring assembly 110 with the inner tube 130 positioned within the outer cutting tube 125. With the device in the "open" state shown in FIG. 9, the distal edge of the inner tube 130 is located proximal to the internal taper of the outer cutting tube 125. The inner tube 130 has an external diameter D3 that is smaller than the diameter D2 (at the beginning of the taper) but larger than diameter D1 (at the end of the taper). When distal linear movement of the inner tube 130 occurs relative to the outer cutting tube 125, the distal edge of the inner tube 130 moves toward the distal edge of the outer cutting tube 125 (or vice-versa). This is the relative position of the inner tube 130 and outer cutting tube 125 in the device's "closed" state. When in the closed state, the internal taper of the outer cutting tube 125 interferes with the outer diameter of the inner tube 130, resulting in the inner tube 130 having a relatively reduced diameter at a distal region of the inner tube 130. The slot 620 accommodates the reduction in diameter of inner tube 130. The reduction in diameter creates a compressive force on a material cored by the distal cutting features of the outer cutting tube 125 and contained within the inner tube 130, as described more fully below.

An exemplary use of the device is now described. The device is first placed in the "open" state such that the inner tube 130 is retracted into the outer tube 125, as was shown in FIG. 8. As discussed above, the device can be placed in the open state by actuating the handle 105, such as by rotating the first handle component 115 counterclockwise relative to the second handle component 120. The use of the device is described in the context of the removal of bone material from a patient during a surgical procedure. In an embodiment, the device is used to obtain core samples from the ilium of the pelvis, such as in the region of the posterior or anterior iliac crest. The device can be used in other skeletal regions, particularly those having repositories of cancellous bone. The device can be used in osseous and osseous cartilaginous regions of the body, as well as other locations of the body.

A cortical defect or pathway can first be formed using a separate, but associated, device. The physician inserts the distal end of the coring assembly 110 through the pathway and into the cancellous bone. The tapered outer walls of the outer cutting tube 125 can reduce the potential for penetrating cortical walls of bone with glancing or low angle contact. A physician grasps the device by the handle 105 and applies a forward pressure through the distal edge 605 of the outer tube 125 against the cancellous bone. The physician can impart an oscillating rotational movement to the distal edge 605 by reciprocal rotation the handle 105. As mentioned, the handle 105 can be configured to lock into the open position so that the device does not inadvertently transition to the closed position during this step. The oscillating rotation of the device effects micro-fracturing of the cancellous trabeculae. The sharpened distal edge 125 of the outer tube 125 and the teeth 610 facilitate such micro-fracturing. In this manner, a distal region of the coring assembly 110 penetrates into the cancellous bone. A plug of cancellous bone is now positioned within the distal region of the coring assembly 110 as a result of the coring assembly's penetration into the bone. That is, a plug or piece of cancellous bone that substantially conforms to the inner shape of the coring assembly is positioned within the inner tube 130. The piece can have various shapes.

After a desired depth of cancellous penetration is achieved, the physician/surgeon can stabilize the second handle component 120 with a first hand while rotating the first handle component 115 with the second hand, transitioning the device into the closed state. Any portion of the coring assembly 110, such as the outer cutting tube 125, can have one or more indicia to assist in identifying the depth of penetration. In an embodiment, an audible and/or tactile detent 235 can be associated with the device being moved to a fully closed position. As discussed above, when the device moves to the closed state, the distal edge of the inner tube 130 moves toward the distal edge of the outer cutting tube 125. The internal taper of the outer cutting tube 125 interferes with the outer diameter of the inner tube 130 to cause the inner tube 130 to annularly constrict or reduce in diameter a distal region of the inner tube 130. The reduction in diameter or annular constriction of inner tube 130 creates a compressive force on the sample of cancellous bone that is present within tube 130.

The compressive force secures or stabilizes the cored cancellous bone. The instrument is then rotated and/or tensioned to shear the bone at the terminus of the instrument. The device is subsequently withdrawn from the bone while the bone sample remains within the inner tube 130. The withdrawal of the device from the bone can be performed with or without continued rotation of the handle 105.

As mentioned, the outer cutting tube 125 has fenestrations 615 that align with a slot 620 in the inner tube 130. The cancellous bone accumulated within the inner tube 130 (which can be one or more plugs of bone) can be observed through the fenestrations 615 and the slot 620. It should be appreciated that the procedure can be performed multiple times to collect a plurality of samples within the inner tube 130 wherein the samples are positioned in sequence within the inner tube 130. The operator can visually verify the quantity of samples within the inner tube by looking through the fenestrations in the outer tube.

Once a sample or samples are collected within the inner tube 130, the cored and sheared material can be extracted. In an embodiment, this is accomplished by using a tamp or plunging member 1005 that interfaces with the cored material within the device (see FIG. 10). The device is first moved to the open state. The tamping member 1005 comprises an elongated, rod-like plunger that fits into a longitudinal bore or cannula that runs the entire length of the core sample device (through the handle 105 and the coring assembly 110). The tamping member 1005 is inserted into the longitudinal bore (such as through a hole at the proximal end of the handle 105) to push the cored bone sample(s) out of the inner tube 130. In this manner, the sample(s) are ejected from the coring assembly 110.

In at least some cases it may be beneficial to remove or create a defect in the cortical bone prior to using a bone coring device. For example, cancellous bone, which is located deep to cortical bone, may be acquired for diagnostic or bone grafting purposes. As such, penetrating the bone in order to remove or create a defect in some of the overlaying cortical bone can assist with accessing underlying cancellous bone tissue for coring.

Figure 11A:
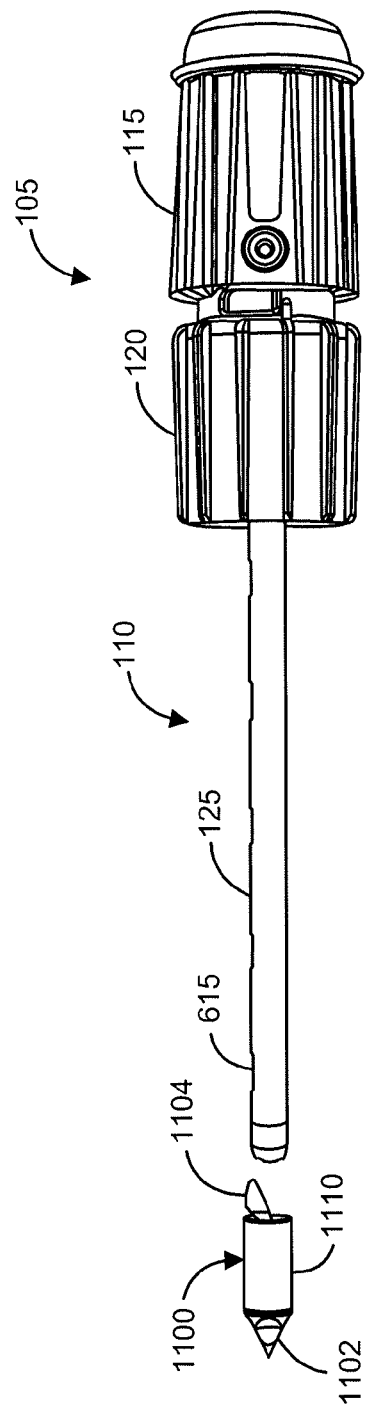
FIG. 11A shows an embodiment of a removable tip device disengaged from a distal end of the core sample device.
Figure 11B:
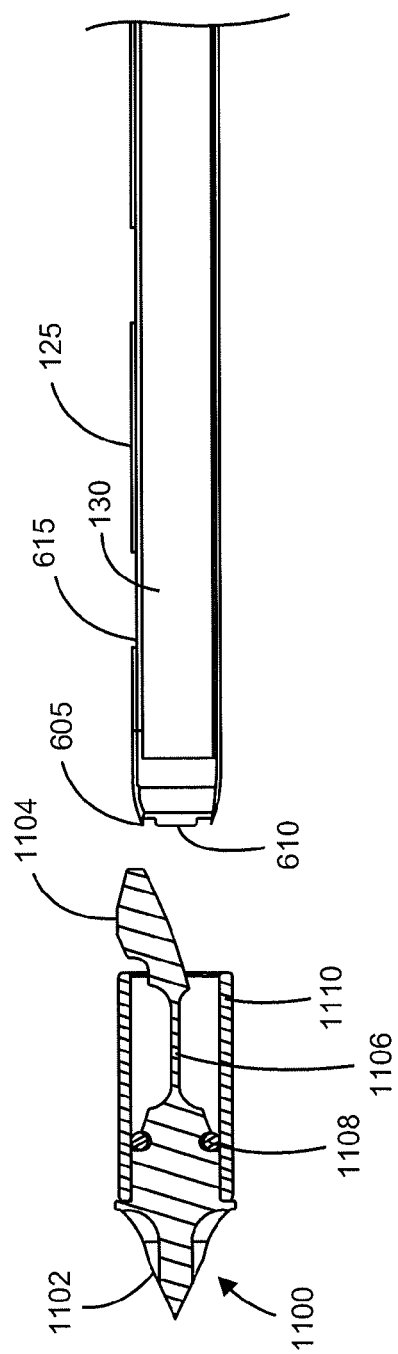
FIG. 11B shows a partial cross-section view of the removable tip device shown in FIG. 11A disengaged from the distal end of the core sample device.

FIGS. 11A and 11B show an embodiment of a removable tip device 1100 disengaged from a distal end of a bone coring device. The removable tip device 1100 can include a bone penetration feature 1102 at a distal end that can penetrate bone and, for example, either remove or create a defect (i.e., crack, chip, etc.) in one or more layers of bone, including cortical bone. In addition, the removable tip device 1100 can include a securing feature 1104 that is configured to releasably engage a distal end of a bone coring device, such as the core sample device described herein. Although the removable tip device 1100 is shown and described as being configured to removably secure to the core sample device described herein, the removable tip device 1100 can be removably secured to any number of a variety of bone coring system and devices.

The bone penetration feature 1102 can include a variety of features, including a sharp distal cutting tip that can allow the removable tip device 1100 to penetrate bone by displacing and removing portions of the cortical surface. In addition, the bone penetration feature 1102 can create a variety of defects or bone removal formations, such as creating an approximately circular hole through the cortical bone layer. Some bone penetration features 1102 may have features similar to a trephine surgical instrument. Additionally, the bone penetration feature 1102 can be made out a medical grade material that is durable enough to withstand penetrating and creating defects in bone, such as various steel alloys, ceramics or structural plastics.

Figure 12A:
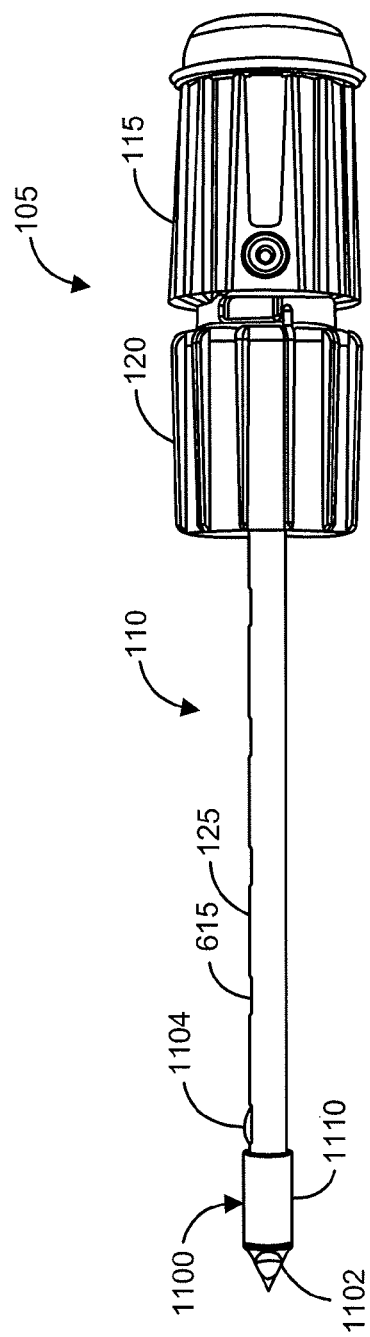
FIG. 12A shows an embodiment of the removable tip device shown in FIG. 11A secured to the distal end of the core sample device.
Figure 12B:
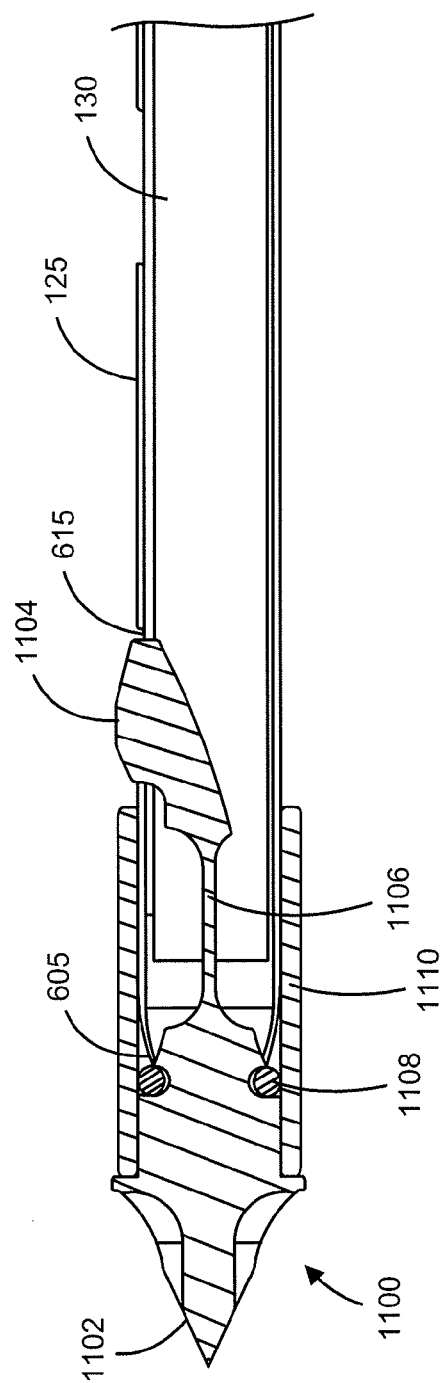
FIG. 12B shows a partial cross-section view of the removable tip device shown in FIG. 11A secured to the distal end of the core sample device.

During attachment of the removable tip device 1100 to the coring assembly 110 of the core sample device, the securing feature 1104 can be inserted into the distal end of the coring assembly 110 and an outer sleeve 1110 of the removable tip device 1100 can slide over an outer surface of the coring assembly 110. The securing feature 1104 can continue to advance into the coring assembly until the securing feature 1104 engages a fenestration 615, as shown in FIGS. 12A and 12B, which locks the removable tip device 1100 to the distal end of the coring assembly 110. The securing feature 1104 is shown in FIGS. 11A-12B as having a displaceable tab or push button configuration, however, any number of releasably engaging features can be implemented into the removable tip device 1100 for securing to the distal end of the core sample device.

Once the removable tip device 1100 is secured or locked to the end of the coring assembly 110, a user can position the bone penetration feature 1102 in contact with bone for creating a cortical surface defect. The outer sleeve 1110 can engage the outer surface of the coring assembly 110 and assist in securing the position of the removable tip device 1100 relative to the coring assembly 110. This can assist in efficiently translating applied forces, such as rotational and translational forces, from the handle 105 and coring assembly 110 to the bone penetrating feature 1102, which can efficiently either remove or create a defect in bone layers. The outer sleeve 1110 can be configured to provide stabilization of the removable tip device 1100 relative to the coring assembly 110 during use and when applying various loads (i.e., torsional loads, such as angular displacing loads, longitudinal loads, etc.) to at least the coring assembly 110 and removable tip device 1100.

The removable tip device 1100 can be released from the coring assembly 110 by activating the securing feature 1104, which can disengage the securing feature 1104 from the coring assembly 110. For example, the user can push down on the securing feature 1104 that is extending through the fenestration 615 and concurrently withdraw the removable tip in the distal direction until the removable tip device 1100 is completely disengaged, as shown in FIGS. 11A and 11B. This can allow a user to then use the core sample device to core and remove bone that has been at least partially exposed due to penetrating the bone with the removable tip device 1100.

In addition, the securing feature 1104 can be configured to engage the fenestration 615 such that movement between the securing feature 1104 and the fenestration 615 is minimized. For example, the securing feature 1104 can engage the fenestration 615 such that when either a torsional or longitudinal force is applied to the core sample device there is minimal movement experienced between the securing feature 1104 and the fenestration 615. This can assist in efficiently transmitting either the torsional and/or longitudinal force applied to the core sample device to the bone penetration feature 1102 for efficiently either removing or creating a defect in bone layers.

Some embodiments of the removable tip device 1100 can include a deformable and/or deflectable element 1106 that can extend from the securing feature and assist in engaging and disengaging the securing feature 1104 to the distal end of the bone coring device. For example, the deformable/deflectable element 1106 can deform or deflect in response to a force applied to the securing feature 1104, which can allow the securing feature 1104 to disengage from the fenestration 615 and remove the removable tip device 1100 from the distal end of the coring assembly 110.

In addition, some embodiments of the deformable/deflectable element 1106 can assist in transmitting torsional loads from the coring assembly 110 to the bone penetrating feature 1102. This can allow rotational forces that have been applied to the core sample device, via manipulation of the handle 105, to be efficiently transmitted to the bone penetrating feature 1102, such as for either removing or creating a defect in bone, such as cortical bone.

For example, the deformable element 1106 can have an asymmetric cross-sectional geometry, or I-beam configuration, that has a thickness (i.e., a linear dimension associated with its cross section in the plane of deflection) that is smaller than its width (i.e., a linear dimension associated with a plane perpendicular to its plane of deflection). This I-beam configuration can provide sufficient rigidity for transmitting torsional loads from the rotation of the coring assembly 110 (i.e., via the securing feature 1104 engaged with the fenestration 615) to the bone penetrating feature 1102, while also requiring relatively low loading requirements to disengage the securing feature 1104 from the fenestration 615.

Some embodiments of the removable tip device 1100 can include a protective element 1108 configured to provide a protective surface for a distal feature(s) of the bone coring device, such as the teeth 610 or the distal edge 605. As shown in FIG. 12B, the protective element 1108 can be positioned within the removable tip device 1100 such that when the removable tip device 1100 is secured to the distal end of the coring assembly 110, the protective element 1108 is resting against or adjacent to the distal feature of the core sample device. For example, a groove in the removable tip device 1100 can assist in securing the position of the protective element 1108.

The protective element 1108 can provide a protective surface for the distal feature during use of the core sample device, such as when either a longitudinal or torsional load is applied to the core sample device for deforming or removing one or more layers of bone. In addition, the protective element 1108 can be made out of a compliant material that can allow the distal feature to contact and displace portions of the protective element 1108, such as during the applied loads, without causing damage to the distal feature(s), which would otherwise blunt or deform sharp, thin, distal features.

For example, the protective element 1108 can have an o-ring configuration, as shown in FIGS. 11B and 12B. In addition, the protective element 1108 can be made out of one or more of a variety of materials, including compliant and durable polymers (i.e., PTFE) that can provide protection to the distal feature of the core sample device while also being resistant to tearing or shredding, such as during applications of longitudinal and torsional loads to the coring sample device and removable tip device 1100.

The removable tip device 1100 can include a variety of features for assisting a user in either deforming or removing a layer of bone. Additionally, the removable tip device 1100 can include one or more features that can assist with mitigating unintended excessive penetration of the removable tip device 1100 into bone, such as a collar or shoulder stop adjacent the proximal end of the removable tip device 1100 or bone penetration feature 1102.

Although embodiments of various methods and devices are described herein in detail with reference to certain versions, it should be appreciated that other versions, embodiments, methods of use, and combinations thereof are also possible. Therefore the spirit and scope of the tissue (e.g. bone) coring device should not be limited to the description of the embodiments contained herein.

What is claimed:

1. A removable tip device configured to releasably engage a bone coring device, the removable tip device comprising:
   an outer sleeve defining an interior sized to slide over an outer surface of a distal end of the bone coring device, the outer sleeve having a distal end region and a proximal end region;
   a bone penetration feature extending from the distal end region of the outer sleeve, the bone penetration feature being a sharp distal cutting tip configured to penetrate a layer of bone;
   a compliant protective element configured to be positioned within the interior of the outer sleeve and resting against or adjacent to a distal cutting edge of the bone coring device, the protective element configured to provide a protective surface for the distal cutting edge of the bone coring device so as to prevent damage to the distal cutting edge during application of a load against the compliant protective element by the distal cutting edge; and
   a securing feature configured to extend from the proximal end region of the outer sleeve, the securing feature configured to releasably engage the distal end of the bone coring device.

2. The removable tip device of claim 1, wherein the sharp distal cutting tip is configured to penetrate a layer of cortical bone.

3. The removable tip device of claim 1, wherein the securing feature is a push button or tab configured to releasably engage a fenestration along the distal end of the bone coring device.

4. The removable tip device of claim 3, wherein the securing feature is sized to insert within the fenestration such that movement of the engaged securing feature relative to the fenestration is minimized for assisting in transmitting torsional loads from the bone coring device to the bone penetration feature.

5. The removable tip device of claim 1, further including a deformable element configured to extend from the securing feature to assist in at least one of engaging and disengaging the securing feature to the distal end of the bone coring device.

6. The removable tip device of claim 5, wherein the deformable element has an asymmetric cross-sectional geometry that is configured to transmit torsional loads from the bone coring device to the bone penetration feature.

7. The removable tip device of claim 1, wherein the compliant protective element is an o-ring.

8. The removable tip device of claim 1, wherein the outer sleeve is configured to stabilize the removable tip device relative to the bone coring device at least when a torsional load or a longitudinal load is applied to the bone coring device.

9. The removable tip device of claims 5, wherein the deformable element has a thickness and a width, wherein the thickness is smaller than the width forming an I-beam cross-sectional configuration.

10. The removable tip device of claim 9, wherein the I-beam cross-sectional configuration provides sufficient rigidity for transmitting torsional loads to the bone penetrating feature while requiring relatively low load to disengage the securing feature from the fenestration.

11. The removable tip device of claim 1, further comprising a groove formed within the interior of the outer sleeve, the groove configured to receive the compliant protective element within the outer sleeve.

12. The removable tip device of claim 1, wherein a proximal-facing portion of the compliant protective element is configured to contact the distal cutting edge of the outer cutting tube and displace when a load is applied against the compliant protective element by the distal cutting edge.

13. The removable tip device of claim 1, wherein the compliant protective element is formed of a polymer.

14. The removable tip device of claim 1, wherein the compliant protective element is resistant to tearing or shredding during application of a load against the compliant protective element by the distal cutting edge.

* * * * *